US00PP12678P2

(12) United States Plant Patent
Westhoff

(10) Patent No.: US PP12,678 P2
(45) Date of Patent: Jun. 4, 2002

(54) LOBELIA PLANT NAMED 'WESSTAR'

(75) Inventor: Heinrich Westhoff, Südlohn-Oeding (DE)

(73) Assignee: Josef+Heinrich Westhoff Gartenbau-Spezialkulturen, Sudlohn-Oeding (DE)

( * ) Notice: Subject to any disclaimer, the term of this patent is extended or adjusted under 35 U.S.C. 154(b) by 0 days.

(21) Appl. No.: 09/324,081

(22) Filed: Jun. 1, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

PP221 P * 1/1937 Johnson ..... Plt./263
PP11,043 P * 8/1999 Churchus ..... Plt./263

OTHER PUBLICATIONS

GTITM UPOVROM Citation for 'Wesstar' as per QZ PBR 960859; Aug. 7, 1996.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinctive cultivar of Lobelia, *Lobelia erinus L.,* plant named 'Wesstar', characterized by its cascading and rounded plant habit; short internodes; dense and bushy plant form; vigorous growth habit; dark green leaves; and intense blue-colored flowers.

2 Drawing Sheets

BACKGROUND OF THE INVENTION

The present Invention relates to a new and distinct cultivar of Lobelia plant, botanically known as *Lobelia erinus L.,* and hereinafter referred to by the cultivar name 'Wesstar'.

The new Lobelia is a product of a planned breeding program conducted by the Inventor in Sudlohn-Oeding, Germany. The new Lobelia originated from a cross made by the Inventor of the *Lobelia erinus L.* cultivar 'Azuro', disclosed in U.S. Plant Pat. No. 10,758, as the female, or seed, parent with an unnamed selection of *Lobelia erinus L.* as the male, or pollen, parent.

Asexual reproduction of the new cultivar by cuttings in Sudlohn-Oeding, Germany, has shown that the unique features of this new Lobelia are stable and are reproduced true to type in successive propagations.

SUMMARY OF THE INVENTION

Plants of the cultivar 'Wesstar' have not been observed under all possible environmental conditions. The phenotype may vary somewhat with variations in environment such as temperature and light and fertility level without, however, any variance in genotype.

The following traits have been repeatedly observed and are determined to be the unique characteristics of the new Lobelia:

1. Cascading and rounded plant habit.
2. Short internodes, dense and bushy plant form.
3. Vigorous growth habit.
4. Dark green leaves.
5. Intense blue-colored flowers.

The following characteristics differentiate the new Lobelia from the female parent, the cultivar 'Azuro':

1. Plants of the new Lobelia have shorter internodes than plants of the cultivar 'Azuro'.

2. Plants of the new Lobelia have larger and more rounded leaves than plants of the cultivar 'Azuro'.

The following characteristics differentiate the new Lobelia from the male parent, the unnamed selection of *Lobelia erinus L.:*

1. Plants of the new Lobelia are denser than plants of the unnamed selection of *Lobelia erinus L.*.

2. Flowers of plants of the new Lobelia are lighter blue in color with a more intense white eye than flowers of plants of the unnamed selection of *Lobelia erinus L.*.

3. Flower of plants of the new Lobelia face upright or outward and are not pendulous like flowers of the unnamed selection of *Lobelia erinus L.*.

BRIEF DESCRIPTION OF THE PHOTOGRAPHS

The accompanying colored photographs illustrate the overall appearance and flower color of the new Lobelia, showing the colors as true as it is reasonably possible to obtain in colored reproductions of this type. Colors in the photographs may differ slightly from the color values cited in the detailed botanical description which accurately describe the actual colors of the new Lobelia.

The photograph on the first sheet comprises a side perspective view of a typical hanging basket of the new Lobelia.

The photographs on the second sheet comprise close-up views of typical flowers (top) and leaves (bottom) of the new Lobelia (left) and 'Azuro' (right).

DETAILED BOTANICAL DESCRIPTION

In the following description, color references are made to The Royal Horticultural Society Colour Chart except where general terms of ordinary dictionary significance are used. Plants used for the description were grown under greenhouse conditions which closely approximate commercial production conditions in Sudlohn-Oeding, Germany. Plants used for the descriptions were grown as one plant per 12-cm container or three plants per 25-cm hanging basket container and were about 10 weeks from planting rooted cuttings.

Botanical classification: *Lobelia erinus L.* cultivar 'Wesstar'.

Parentage:

*Female parent.*—*Lobelia erinus L.* cultivar 'Azuro', disclosed in U.S. Plant Pat. No. 10,758.

*Male parent.*—Unnamed selection of *Lobelia erinus L.,* not patented.

Propagation:

*Type.*—By cuttings.

*Time to initiate roots.*—About two weeks.

*Root description.*—Fine, fibrous and well-branched.

Plant description:

*Plant form.*—Cascading and rounded perennial flowering plant with numerous intense blue-colored flowers. Freely branching with lateral branches forming at every node. Appropriate for 12-cm containers and 25-cm hanging basket containers.

*Growth habit.*—Lateral shoots outwardly spreading, plants uniform and eventually becoming spherical in overall shape. Vigorous.

*Plant height.*—About 10 to 14 cm.

*Plant diameter.*—About 20 cm.

*Stem description.*—Main branch length: About 40 cm. Main branch diameter: About 2 mm. Lateral branch length: About 27 cm. Lateral branch diameter: About 1.2 mm. Internode length: About 2.5 to 3.3 cm. Texture: Smooth. Color: 146A; young stems and shoot apices with anthocyanin, close to 172B. Cross-section: Square.

*Foliage description.*—Arrangement: Simple, alternate, sessile. Aspect: Mostly flat. Texture: Smooth. Basal leaves: Length: About 3.3 cm. Width: About 3.3 cm. Shape: Rounded, ovate. Apex: Rounded. Base: Attenuate. Margin: Crenate. Mid-plant leaves: Length: About 5.5 cm. Width: About 1.5 cm. Shape: Linear to narrowly ovate. Apex: Rounded. Base: Attenuate. Margin: Crenate, fewer notches than basal leaves. Apical leaves: Length: About 4.9 cm. Width: About 1 cm. Shape: Lanceolate. Apex: Nearly acute. Base: Attenuate. Margin: Entire. Color, all leaves: Young foliage, upper surface: 146B. Young foliage, lower surface: 148A with slight anthocyanin, 172B, on basal leaves. Mature foliage, upper surface: More green than 147A. Mature foliage, lower surface: 147B.

Flower description:

*Flower habit.*—Flowers arranged singly at lateral apices. Flowers held outwardly. Flowers persistent. Older flowers are overgrown by new flowers and foliage. Freely and continuously flowering.

*Flower shape.*—Tubular with three larger lower petals and two upright petals, roughly star-shaped.

*Natural flowering season.*—Spring until frost.

*Flower longevity on the plant.*—Longevity of individual flowers is highly dependent on weather conditions. Typically one to two weeks.

*Flowers.*—Diameter: About 2.1 cm. Height: About 2.2 cm. Throat diameter, apex: About 5 mm. Tube length: About 9 mm. Tube diameter, base: About 3 mm.

*Peduncle.*—Strength: Flexible and wiry, flowers held upright or outwardly. Diameter: About 8 to 10 mm. Color: 146A.

*Flower bud.*—Shape: Oblong. Diameter: About 4 mm. Length: About 1.5 cm. Color: Whitish green to whitish blue just before opening.

*Petals.*—Arrangement: Five petals whorled, fused; three larger lower petals and two smaller upper petals. Three lower petals: Shape: Elliptic. Length, above throat: About 1.2 cm. Width: About 7 mm. Two upper petals: Shape: Narrowly oblong. Length, above throat: About 8 mm. Width: About 3 mm. Upper and lower petals: Apex: Cuspidate. Margin: Entire. Texture: Smooth and satiny. Color: When opening, upper surface: 95B. When opening, lower surface: 94D. Fully opened, upper surface: 95C, at base, 95A; overall color fading to 96D. Fully opened, lower surface: 96C to 96D. Throat: White, 155D, background; with lavender, 79B, spots and two green/yellow, 143B, basal stripes; at the end of the basal stripes of the lower petals, there are two white, 155D, spots, about 3 by 1.5 mm in size and below these spots are three small dark blue, 95A, spots, about 1 mm in diameter.

*Sepals.*—Arrangement: Whorled, fused into a calyx, star-shaped. Shape: Narrowly lanceolate to needle-like. Quantity per flower: Five. Length: About 1.3 cm. Width: About 1.5 mm. Apex: Acute to acuminate. Margin: Entire. Texture: Smooth. Color: Upper surface: 146A. Lower surface: 147B.

*Reproductive organs.*—Stamens: Quantity: Five, fused. Filament color: Whitish blue, 97D. Anther length: About 2 mm. Anther width: About 1 mm. Anther color: 79A. Pollen amount: Moderate. Pollen color: 3B. Pistils: Quantity: One. Pistil length: About 1.1 cm. Stigma shape: Two kidney-shaped parts, fused, appeared rounded. Stigma color: 83B. Style length: About 7 mm. Style color: 144C. Ovary color: 146A.

Disease resistance: Resistance to known pathogens of Lobelia has not been observed.

Weather tolerance: Good tolerance to wind and rain.

Seed production: Seed production has not been observed.

It is claimed:

1. A new and distinct cultivar of Lobelia, *Lobelia erinus L.,* plant named 'Wesstar', as illustrated and described.

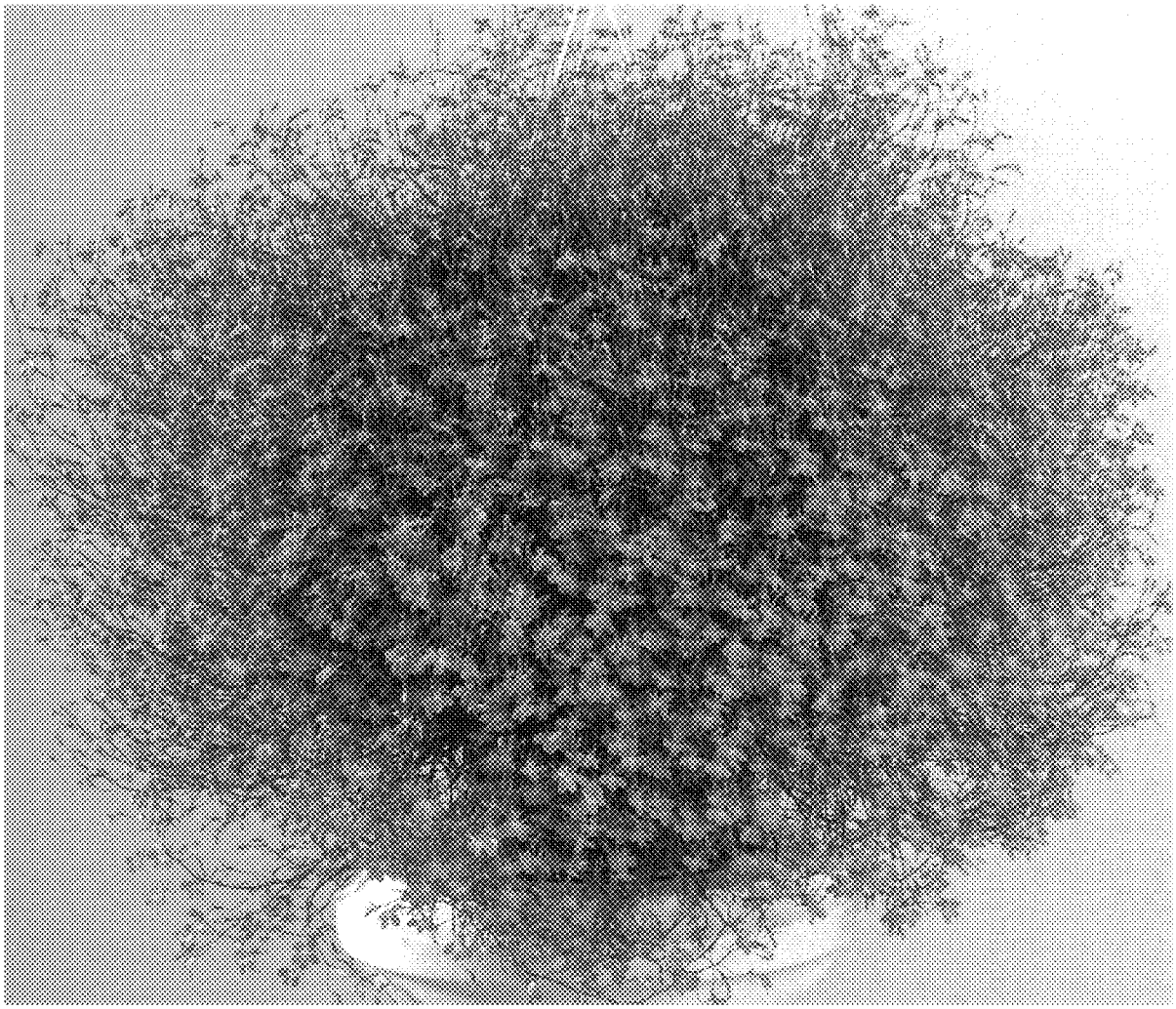

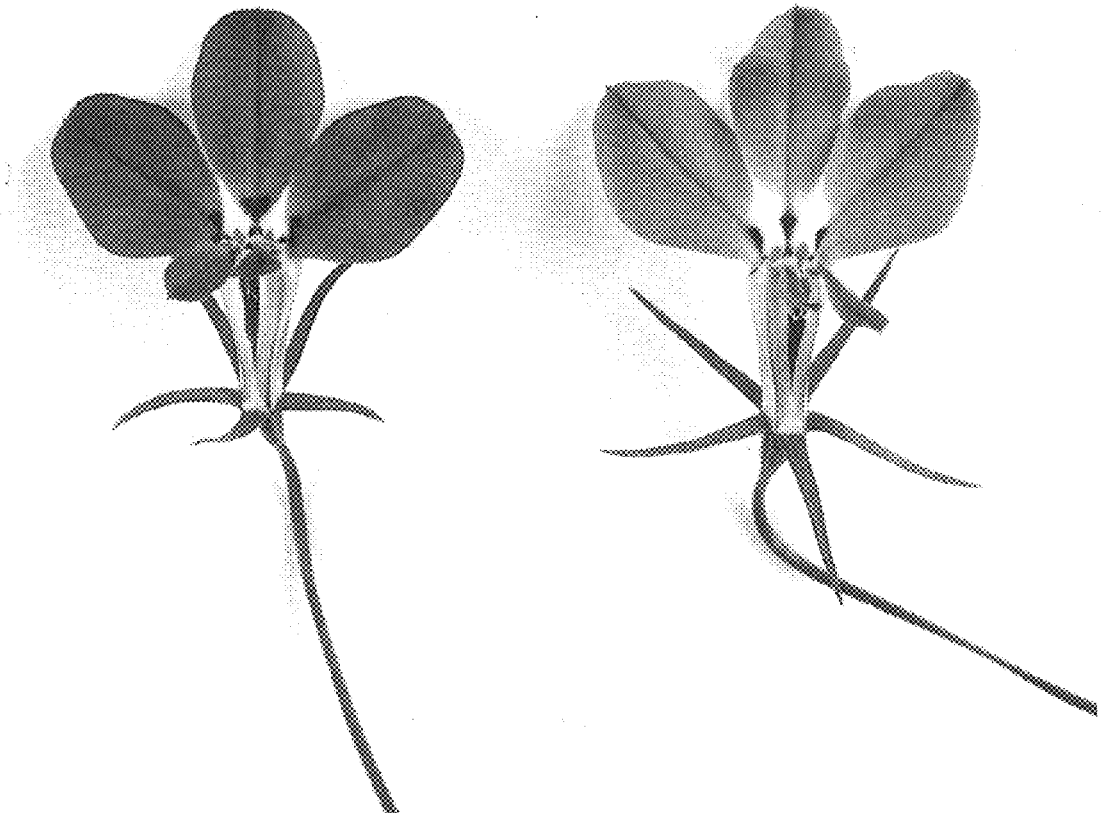
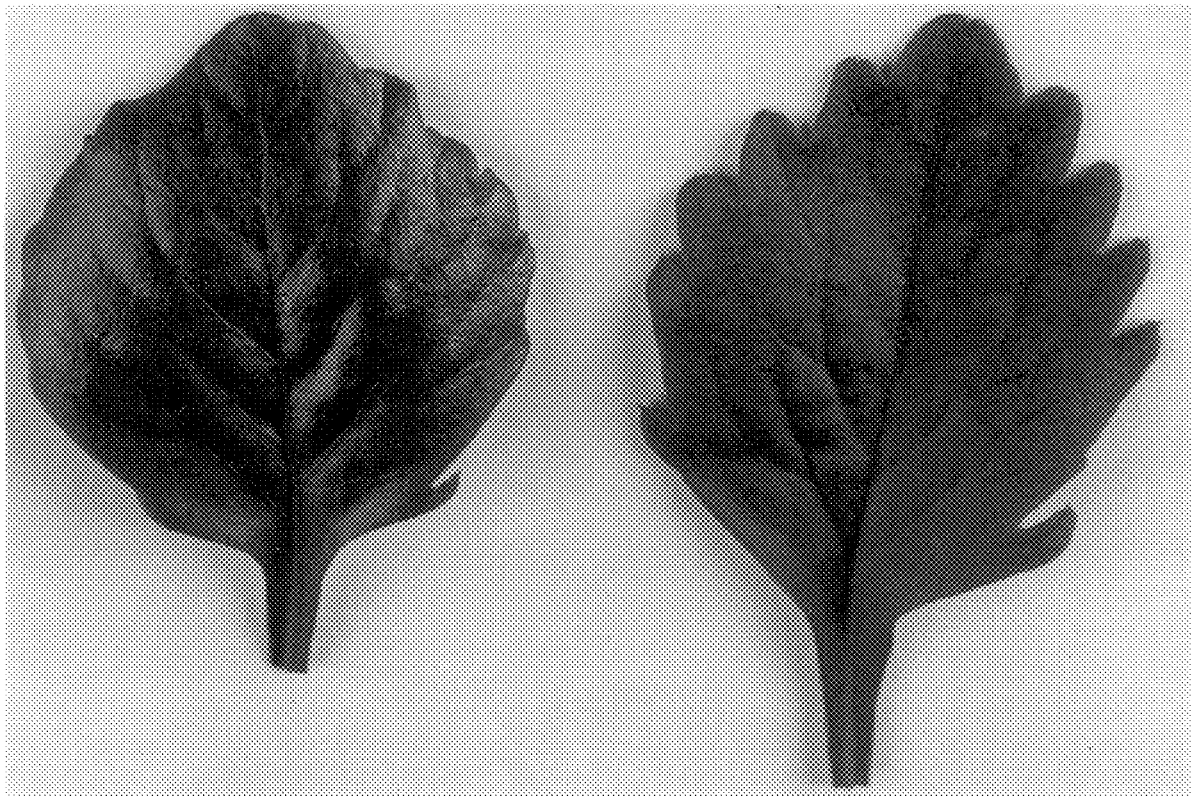

* * * * *